(12) United States Patent
Lott

(10) Patent No.: US 10,506,320 B1
(45) Date of Patent: Dec. 10, 2019

(54) DYNAMIC EARPHONE TIP

(71) Applicant: Phillip Dale Lott, Charlotte, TN (US)

(72) Inventor: Phillip Dale Lott, Charlotte, TN (US)

( * ) Notice: Subject to any disclaimer, the term of this patent is extended or adjusted under 35 U.S.C. 154(b) by 0 days.

(21) Appl. No.: 16/244,789

(22) Filed: Jan. 10, 2019

(51) Int. Cl.
| H04R 25/00 | (2006.01) |
| H04R 1/10  | (2006.01) |
| A61F 11/10 | (2006.01) |

(52) U.S. Cl.
CPC ............ *H04R 1/1016* (2013.01); *A61F 11/10* (2013.01); *H04R 1/1091* (2013.01); *H04R 25/60* (2013.01); *H04R 25/65* (2013.01); *H04R 25/652* (2013.01); *H04R 25/656* (2013.01); *H04R 2460/15* (2013.01)

(58) Field of Classification Search
CPC .... H04R 1/1016; H04R 1/1083; H04R 25/60; H04R 25/65; H04R 25/652; H04R 25/656; H04R 2460/11; H04R 2460/15; A61F 11/10
USPC ............... 381/322, 324, 325, 328, 329, 380; 128/864, 865; 181/129, 130, 135
See application file for complete search history.

(56) References Cited

U.S. PATENT DOCUMENTS

| 2,535,258  | A   | 12/1950 | Bland       |              |
|------------|-----|---------|-------------|--------------|
| 3,602,654  | A   | 8/1971  | Victoreen   |              |
| 4,962,537  | A   | 10/1990 | Basel et al.|              |
| 5,483,027  | A   | 1/1996  | Krause      |              |
| 7,227,968  | B2* | 6/2007  | van Halteren| H04R 25/652  |
|            |     |         |             | 381/322      |
| 7,362,875  | B2  | 4/2008  | Saxton et al.|             |
| 7,425,196  | B2* | 9/2008  | Jorgensen   | H04R 25/456  |
|            |     |         |             | 600/25       |
| 7,639,831  | B2  | 12/2009 | Hagberg     |              |
| 7,779,844  | B2  | 8/2010  | Purcell et al.|            |
| 8,280,093  | B2  | 10/2012 | Siahaan et al.|            |
| 8,340,310  | B2  | 12/2012 | Ambrose et al.|            |
| 8,391,534  | B2  | 3/2013  | Ambrose et al.|            |
| 8,548,181  | B2* | 10/2013 | Kraemer     | H04R 1/1016  |
|            |     |         |             | 381/150      |
| 8,631,801  | B2  | 1/2014  | Keady       |              |
| 8,657,064  | B2  | 2/2014  | Staab et al.|              |
| 8,678,011  | B2  | 3/2014  | Goldstein et al.|          |
| 9,358,568  | B2  | 5/2016  | van Hal     |              |
| 10,145,107 | B2  | 8/2018  | Kirsch et al.|             |
| 2013/0114839 | A1* | 5/2013 | Gebert     | H04R 1/1016  |
|            |     |         |             | 381/328      |
| 2013/0136285 | A1 | 5/2013  | Naumann     |              |
| 2013/0251172 | A1 | 9/2013  | Mosseri     |              |

* cited by examiner

*Primary Examiner* — Huyen D Le
(74) *Attorney, Agent, or Firm* — Hall Estill Attorneys at Law; Tyler J. Mantooth

(57) ABSTRACT

An earphone can employ a dynamic tip to seal the ear canal of a user. At least one audio transducing driver may be positioned within a housing that is attached to a dynamic tip. The tip can have a first chamber separated from a second chamber by a constriction ring with sealing material occupying portions of the first chamber and the second chamber.

17 Claims, 5 Drawing Sheets

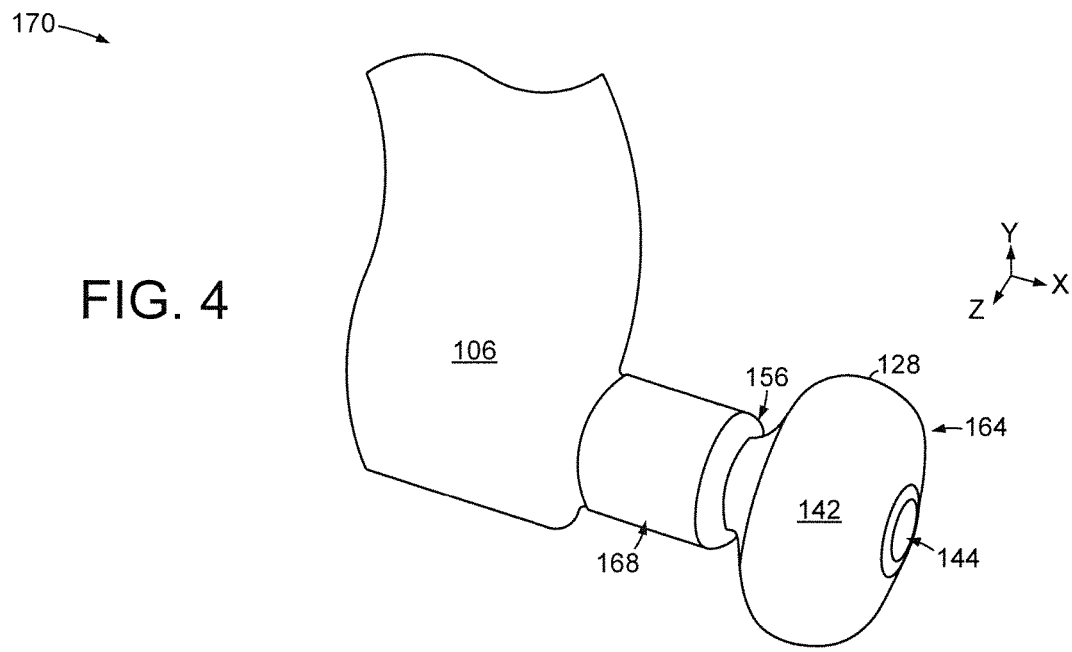
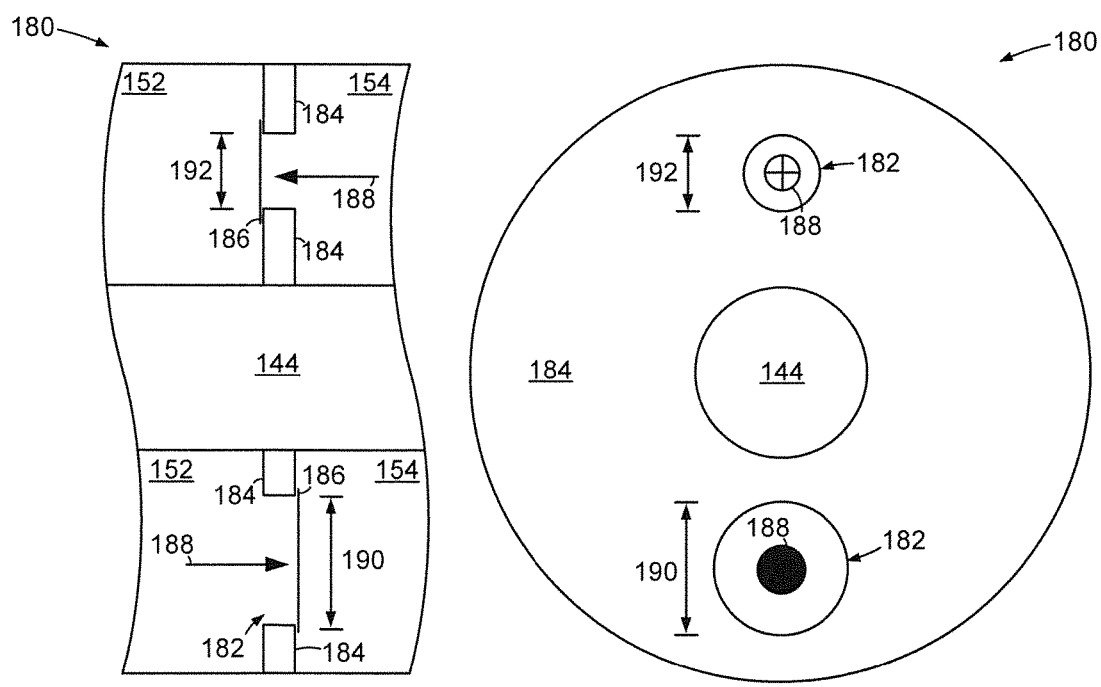

DYNAMIC EARPHONE TIP

SUMMARY

An earphone, or headphone, in accordance with some embodiments, has at least one audio transducing driver positioned within a housing. A tip is attached to the housing and is configured with a sealing section separated from a reservoir section by a constriction band that restricts flow of a sealing material between a first chamber and a second chamber.

In other embodiments, an earphone has at least one audio transducing driver positioned within a housing having an audio nozzle that is attached to a dynamic tip via a retention feature. The tip has first chamber separated from a second chamber by a constriction ring with sealing material occupying portions of the first chamber and the second chamber.

An earphone tip can be utilized, in various embodiments, by attaching a tip to an audio nozzle of a housing with the housing containing at least one audio transducing driver. Squeezing a sealing section of the tip forces sealing material into a first chamber of the tip from a second chamber through a constriction ring. The tip is inserted into an ear canal of a user. The sealing material is then forced out of the first chamber through the metering area of the constriction ring using the modulus of elasticity of the deformable membrane of the tip into the second chamber to inflate the sealing section to a sealing diameter that contacts and seals the ear canal.

BRIEF DESCRIPTION OF THE DRAWINGS

FIG. 4 illustrates portions of an example earphone arranged in accordance with various embodiments.

FIGS. 5A and 5B respectively depict portions of an example tip that can be employed in an earphone in accordance with some embodiments.

DETAILED DESCRIPTION

Various embodiments of the present disclosure are generally directed to an earphone, headphone, or ear plug system with a tip optimized to dynamically change to substantially seal the ear canal of a user.

Since the advent of audio transducers, there has been an industry and consumer push to increase the quality of sound being reproduced. Through the years, a diverse variety of audio reproducing assemblies have positioned one or more acoustic transducers in different locations in, on, or around the ear of a user, with each configuration posing structural and operational challenges along with advantages.

For in-ear sound reproducing assemblies (earphones), the lack of physical space and retention mechanism, compared to over/on ear (headphones), has presented structural challenges that materially degrade the comfort and performance of an earphone. As an example, physically anchoring an earphone has often been counterproductive to sealing the ear canal and efficiently producing optimal audio reproduction performance. That is, while deformable earphone tips have been used to fill the ear canal of a user, jaw movement and sound pressure often act in concert with the elastic characteristics of the tip material to force the earphone out of an efficient acoustic position within the ear.

In other attempts to provide a sustainable ear canal seal for an earphone, bladders, bubbles, or balloons have been constructed that inflate once inserted into the ear canal to physically anchor an earphone while sealing the ear canal. However, consistent inflation and pressurization of an inflatable membrane has been difficult to construct and practically implement in a capacity that allows for high fidelity, efficient audio reproduction. For instance, providing enough pressure to continually inflate a membrane to seal an ear canal can occupy valuable physical real estate in an earphone while requiring user involvement to set, alter, or deflate the membrane. As such, an earphone with an inflatable membrane has exclusively been relatively large, power-hungry, and acoustically inefficient compared to earphones employing elastically deformable tips that seal a user's ear canal.

Accordingly, various embodiments are directed to a deformable earphone tip that has first and second internal chambers separated by a constriction band that allows the tip to dynamically conform to a user's ear canal while allowing internal earphone space to be employed for optimized acoustical characteristics. The dynamic physical capability of a tip allows for easy insertion into an ear canal followed by automatic sealing of the ear canal in response to the modulus of elasticity of the material of the tip, which forces sealing material through the constriction band to enlarge a sealing portion of the tip to contact, and seal, the ear canal.

Figure 1:
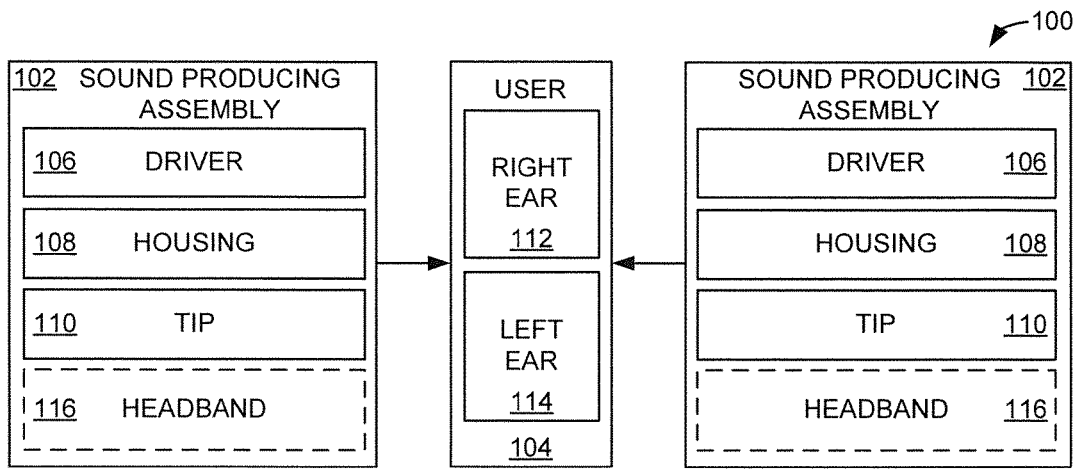
FIG. 1 is a block representation of an example sound reproducing system in which various embodiments may be practiced.

Turning to the drawings, FIG. 1 depicts a block representation of an example sound reproducing system 100 in which various embodiments can be practiced. The system 100 can employ one or more sound reproducing assemblies 102 that provide audible signals to a user 104. Each assembly 102 can have a sealed, or vented, housing 106 in which one or more acoustic transducers (drivers) 108 are positioned. A housing 106, in some embodiments, directs sound from the constituent driver(s) 108 to a nozzle that is shaped to retain a deformable tip 110 while allowing sound to efficiently pass.

Each assembly 102 is directed to being an earphone positioned in the respective right 112 and left 114 ears of a user. However, it is contemplated that the assemblies 102 may be configured as an over-ear, or on-ear, headphone that utilizes one or more headbands 116. The in-ear/earphone arrangement can be characterized by concurrent physical contact of the tip 110 with portions of the ear canal of an ear 112/114 and contact of the housing 106 with portions of the outer ear, such as the concha, tragus, and antihelix.

Figure 2A:
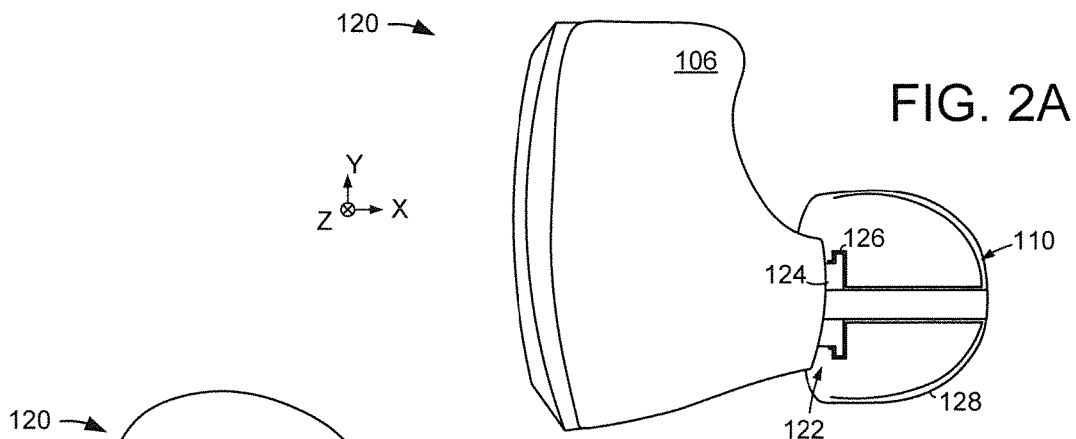
FIGS. 2A and 2B respectively display line representations of portions of an example earphone arranged in accordance with some embodiments.
Figure 2B:
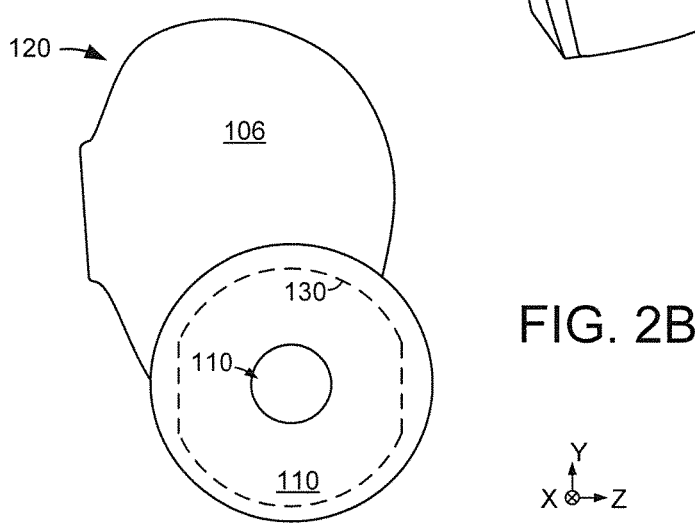

FIGS. 2A and 2B respectively show portions of an example earphone 120 that can be utilized in the sound reproducing system 100 of FIG. 1 in accordance with various embodiments. FIG. 2A is a side view line representation of a single earphone 120 that is used to physically, and acoustically, engage a single ear 112/114 of a user 104. The earphone 120 has a housing 106 that may be two or more attached pieces that position one or more drivers 108 in an acoustically advantageous position relative the ear drum of an ear 112/114.

The physical position of a driver 108 in the housing 106 can be complemented by an audio nozzle 122 where acoustic signals leave the housing 106 and enter an ear canal. The size, shape, and orientation of the audio nozzle 122 is not limited to a particular configuration, but can comprise a retention feature 124 so that a tip 110 can attach to the housing 106. The retention feature 124 may be one or more physical elements, such as a groove, ridge, notch, protrusion, or tab, that physically contacts a nozzle receiver 126 of the tip 110 to retain the tip 110 on the housing 106 throughout insertion, use, and removal of the earphone 120 from a user's ear 112/114. It is contemplated that the housing 106 is configured without a nozzle 122 and/or retention feature 124 and a tip is friction fit onto the housing 106, such as with a textured housing surface.

The front view of FIG. 2B conveys how the tip 110 continuously extends around the audio nozzle 122 to provide a deformable membrane 128 that is configured to physically contact portions of the ear canal of an ear 112/114. The deformable membrane 128 may be any shape, size, or orientation with respect to the audio nozzle 122 and may be made of any elastically deformable material, such as silicone, thermoplastic elastomer, polymer, rubber, foam, or hybrid blends of these materials.

In some embodiments, the deformable membrane 128 has a predetermined, underformed shape, such as oval, circular, hexagonal, or a combination of linear and curvilinear surfaces, as shown by segmented shape 130, in the Y-Z plane. The ability to tune the shape of the deformable membrane 128 in the Y-Z plane can be complemented by a tuned cross-sectional shape of the membrane 128 in the X-Y plane, which can be continuously curvilinear, linear, or any combination of multiple surfaces. By customizing the exterior surface(s) of the deformable membrane 128, the tip 110 can more efficiently be inserted in a user's ear and provide greater ear canal sealing once the elastic material of the membrane 128 expands from the deformation of insertion to exert force on the ear canal.

While the shape, size, and material of the tip 110 can be customized to increase short-term comfort and performance, the structural characteristics of the deformable membrane 128 can degrade over time. For example, the material and shape of the deformable membrane 128 can exert force onto the ear canal once inserted, which increases sound quality and fitment, but alterations to the shape and size of the ear canal in response to jaw movement often work with the force exerted by the membrane 128 to partially, or completely eject the earphone 120 from the user's ear canal. Hence, the characteristics that short-term performance can result in long-term earphone 120 failures.

Figure 3A:
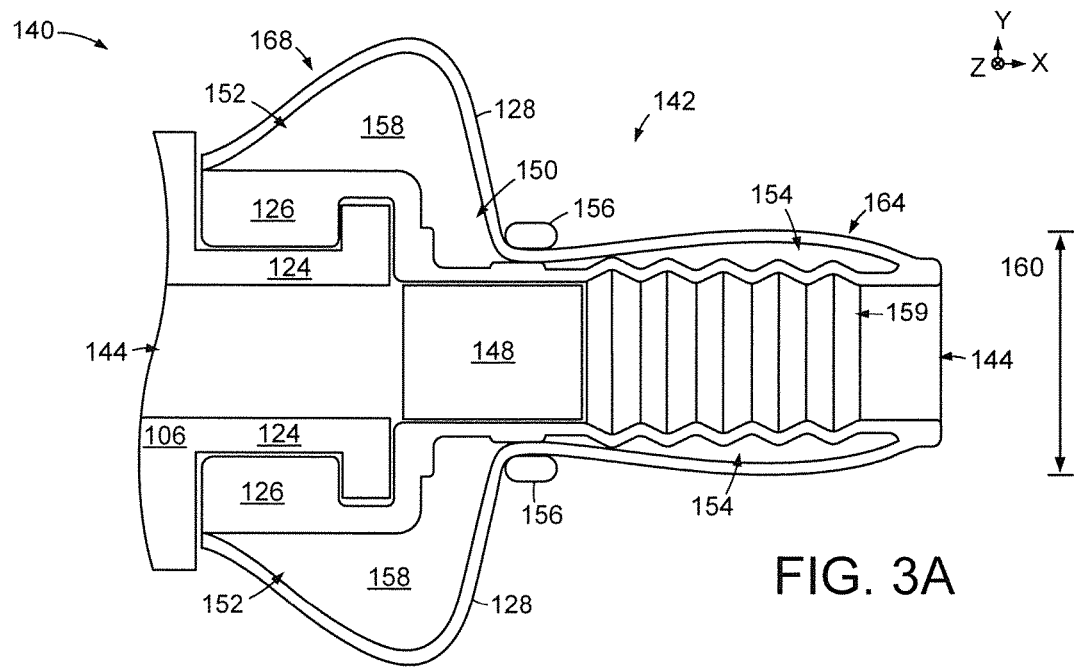
FIGS. 3A-3D respectively show portions of an example earphone tip configured in accordance with assorted embodiments.
Figure 3B:
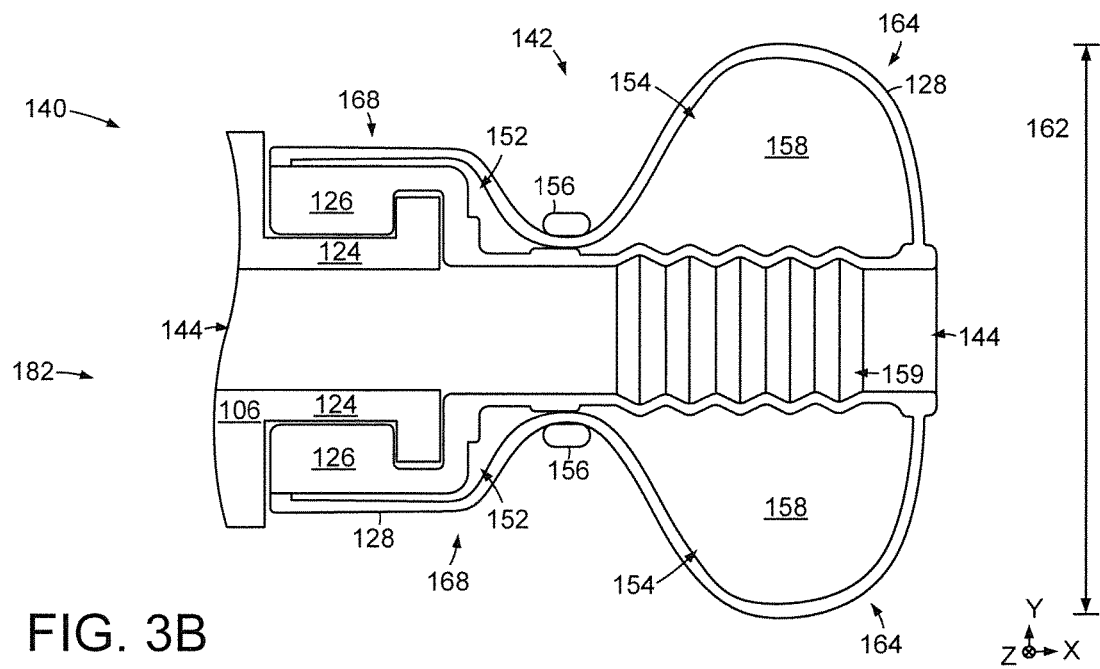
Figure 3C:
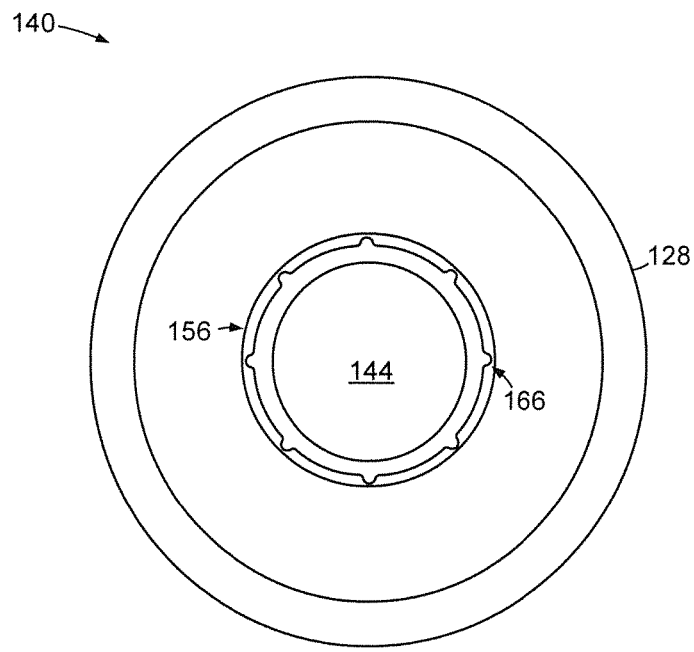

Accordingly, various embodiments are directed to a tip 110 that can dynamically adapt to changes in a user's ear canal to maintain comfort, fit, and audio performance. FIGS. 3A-3C and 3B respectively display portions of an example assembly 140 that can be employed in an earphone, or headphone, to provide optimized ear canal sealing and audio reproduction performance over time.

The cross-sectional illustrations of FIGS. 3A and 3B show how the tip 142 attaches to a retention feature 124 of an audio nozzle 122 of a housing 106 with a nozzle receiver 126. The nozzle 122 and tip 142 each have at least one audio conduit 144 that continuously extends through from the interior of the housing 106 to the ear canal 146 of a user, which allows an unimpeded path for audio signals and air to flow. It is contemplated that at least one conduit 144 is shaped to increase audio and/or airflow performance, such as with a uniform or varying cross-sectional diameter measured in the Y-Z plane. The tuning of the audio conduit 144 can allow for optimized air pressurization and sound pressurization.

The audio conduit 144 may be impeded, in some embodiments, by an attenuating feature 148 that can reduce, or eliminate, the passage of sound and/or air, to the ear canal 146. Such attenuating feature 148 can be located wholly in the tip 142 and serve to practically make the assembly 140 an ear plug or sound mitigating in-ear device. The configuration of the attenuating feature 148 is not limited to a particular design, but can be a single piece, or assembly, that redirects sound away from the ear drum of a user. In the non-limiting embodiment shown in FIG. 3A, the audio conduit 144 is continuously uniform from the housing 106 throughout the tip 142.

The tip 142 further comprises a sealed reservoir 150 that is segmented into a first chamber 152 and a second chamber 154 by a constriction ring 156. The reservoir 150 can be partially, or completely, filled with a sealing material 158 that flows between the chambers 152/154, as controlled by the constriction ring 156. The sealing material 158 may be any substance with a predetermined viscosity, such as a liquid, gas, or gel. For instance, the sealing material 158 can be an oil, styrene, or glycerol, that exhibits a viscosity that holds the material 158 on either side of the constriction ring 156 until a predetermined amount of force is applied to the chamber 152/154 occupied by the material 158. In this way, the viscosity of the sealing material 158 is chosen based on the configuration of the constriction ring 156 to restrict material 158 flow between the chambers 152/154.

The sealed configuration of the chambers 152/154 and constriction ring 156 means that one chamber will have a greater pressure than the other chamber depending on the volume of sealing material in the respective chambers 152/154. The configuration of the constriction ring 156 as a flexible component that adapts to applied force allows for sealing material 158 metering and flow rate control. As such, the constriction ring 156 can be characterized as a metering section that connects the respective chambers 152/154.

The chambers 152 can be any size and shape, but in some embodiments, continuously extends around the audio conduit 144 and can be characterized as a distal chamber 152, proximal the housing 106, and a sealing chamber 154, distal the housing 106. The constriction ring 156 may be a single member, or assembly, that restricts flow of the sealing material 158 between chambers 152/154. That is, the constriction ring 156 may have a biased configuration where so that the sealing material 158 flows at a different rate towards the second chamber 154 than towards the first chamber 152.

In FIG. 3A the tip 142 is in a deflated state where a majority of the volume of the sealing material 158 is located in the first chamber 152 to allow the deformable membrane 128 to collapse to a reduced diameter 160. The deflated state may also be characterized as the reduced membrane diameter 160 without a majority of the sealing material 158 being in the first chamber 152. The tip 142 is arranged with a flexible section 159 that has a plurality of striations allowing the tip 142 to bend and conform to the shape of a user's ear canal while providing a useful audio conduit 144 pointing towards the ear drum of the user.

An inflated tip state is shown in FIG. 3B where the deformable membrane 128 is enlarged from the reduced diameter 160 to a sealing diameter 162. It is noted that the enlarged sealing diameter 162 may be anywhere in the sealing section 164 of the tip 142, extending from the constriction ring 156 to contact the ear canal 146 of a user, as displayed in FIG. 3C. The inflated tip state can be characterized as a majority of sealing material 158 being present in the second chamber 154 and/or the first chamber having a diameter at or below a deflated threshold.

The constriction ring 156 can be characterized as a two-way valve between the chambers 152/154. The ring 156, in the non-limiting embodiment of FIG. 3C, has a plurality of separated protrusions 166 that are shaped to restrict flow through the ring 156. In practice, a user can squeeze the second chamber 154, sealing section 164 aspect of the tip 142 with at least a predetermined amount of force that overcomes the modulus of elasticity of the deformable membrane 128 of the first chamber 152 to flow the sealing material 158 to the first chamber 152 and produce a reduced second chamber diameter 160 that allows for easy insertion of the tip 142 into the ear canal 146.

Figure 3D:
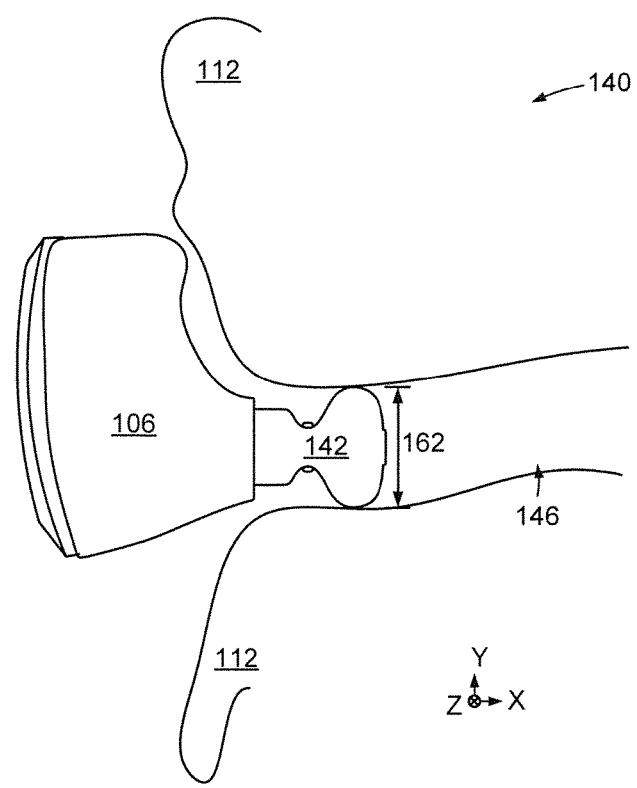

With the constriction ring 156 constructed of an elastic material, which may, or may not, be the same material as the deformable membrane 128, squeezing the second chamber 154 will expand the constriction ring 156 and allow relatively large volumes of sealing material 158 to be quickly moved into the first chamber 152. Once in the first chamber 152, as illustrated in FIG. 3A, the modulus of elasticity of the deformable membrane 128 will automatically exert force onto the sealing material to force sealing material 158 towards the constriction ring 156. In contrast to the squeezing of the second chamber 154 by a user, the application of force via the modulus of elasticity of the deformable membrane 128 that defines the first chamber 152 is more gradual and results in the constriction ring 156 minimally expanding, which allows the protrusions 166 to meter the sealing material flow rate to a predetermined volume conducive to comfortably expanding the second chamber 154, as shown in FIG. 3B, to seal the ear canal 146, as shown in FIG. 3D.

In some embodiments, the constriction ring 156 is configured to close and cut off any flow of sealing material 158 unless a predetermined amount of force is applied to the deformable membrane 128 on either side of the ring 156. Such force-dependent constriction ring 156 allows sealing material to be maintained in either chamber 152/154 for an extended time frame. Conversely, the metering configuration provided by a continual ring opening and metering protrusions 166 allow sealing material to dynamically flow between the chambers 152/154 to provide automatic adaptive ear canal 146 sealing.

Once inside the ear canal 146, the material of the deformable membrane 146 provides some elastic expansion of the sealing section 162. The force of insertion of the tip 142 along with the modulus of elasticity of the deformable membrane, applies force onto the reservoir section that causes the sealing material 158 to breach the constriction ring 156 and flow into the second chamber 154 with a volume that inflates the sealing section 162 so that the deformable membrane 128 contacts, and seals, the ear canal 146.

The perspective view of FIG. 4 conveys an example earphone 150 where a dynamic tip 142 is assembled onto a housing 106. The tip 142 can be selectively attached to, or removed from, the housing 106 to present the sealing section 162 and reservoir section 168 for application of external force. The housing 106 provides ample surface area for physical retention during squeezing of the sealing section 162 and insertion of the tip 142 into the ear canal 146. Once inside the ear canal 146, the housing 106 can be engaged to remove the tip 142 without deflating the sealing section 162.

Although the constriction ring 156 can be considered a two-way valve between the chambers 152/154, the ring 156 may consist of a number of one-way valves 172. FIG. 5 illustrates an example earphone tip 180 configured in accordance with various embodiments to provide controlled flow between the chambers 152/154 with multiple one-way valves. A valve may be constructed in any number of manners, but in some embodiments consists of an orifice 182 extending through a plate 184 with an articulable member 186 that allows sealing material 158 to flow only in one direction through the plate 154, as indicated by solid arrows 188.

It is contemplated that valves can be differently configured within a single earphone tip. Such different configuration is not limited, but can consist of different member 186 materials, shapes, or functions, orifice 182 positions in one or more plates 184, and orifice diameters. The example configuration of FIG. 5A conveys how a sealing material flow can be biased towards the second chamber 154 by making the orifice 182 flowing into the second chamber 154 have a larger diameter 190 than the diameter 192 of the orifice 182 flowing into the first chamber 152.

As a result of the dissimilar valves, the sealing material 158 will remain in the second chamber 154 longer than in the first chamber 152 for a uniform force exerted on the entirety of the tip. The dissimilar valves allow for different sealing material flow rates between the respective chambers 152/154, which provides retention of sealing material 158 in a selected chamber 152/154 for a longer time and/or in response to greater force applied to the deformable membrane 128.

The positioning of multiple valves in a single plate 184 efficiently utilizes space in a tip 180, but is not required as multiple plates, or other sealing material 158 impeding structure, can be positioned within the tip 180 with, or without, a one-way valve. The positioning of the valves in a single plate 184 can provide tuned flow rates between the chambers 152/154.

As shown in the front view of FIG. 5B, positioning the smaller orifice 182 towards the top of the plate 184 allows gravity to make more sealing material 158 available to flow to the second chamber 154 through the larger orifice 182. By placing an orifice 182 towards the outer circumference of the plate 184, the force required to flow sealing material 158 through the orifice 182 will be reduced. The ability to customize the flow rates between internal tip chambers 152/154 allows for optimal dynamic adaptation of the tip 180 for different in-ear applications, such as hearing aids, ear plugs, or sound reproducing monitors.

Figure 6:
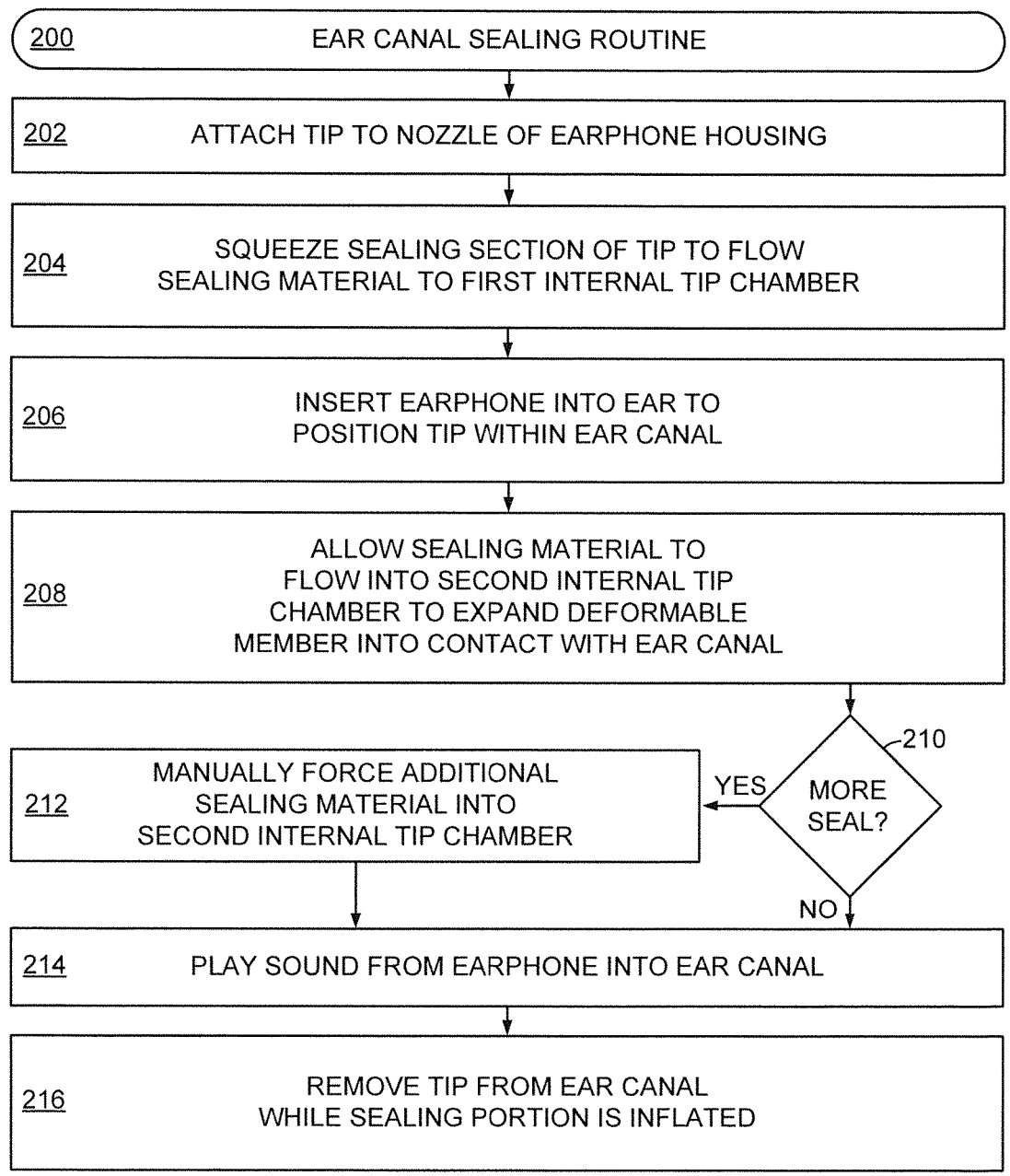
FIG. 6 provides a flowchart of an example ear canal sealing routine that can be carried out by the various embodiments of FIGS. 1-5B.

FIG. 6 is a flowchart of an example ear canal sealing routine 200 that can be performed with the various embodiments of FIGS. 1-5B. Initially, a tip is attached to a nozzle of a housing in step 202. It is contemplated that a tip can be utilized without a housing, such as in the case of an ear plug. Step 202 can consist of engaging a retention feature of a nozzle with a receiver of the tip so that the tip is secured to the housing as a unitary earphone assembly.

Next, step 204 applies force onto the sealing section of the deformable membrane of the tip to induce the flow of sealing material from the second chamber to the first chamber. The squeezing force of step 204 is applied until the sealing section reduces below a predetermined diameter threshold to allow the sealing section to easily and efficiently be inserted into the ear canal in step 206. The insertion of the tip as part of an earphone can coincide with the deformable membrane of the tip expanding to contact the ear canal as a function of the natural elastic characteristics of the material of the deformable membrane in cooperation with the ambient pressures present in the ear canal.

While the deformable membrane may expand and contact the ear canal in step 206, the lack of substantial sealing material in the second chamber of the tip causes an insufficient seal of the ear canal by the tip. That is, the tip can provide a partial, or complete, seal of the ear canal without the sealing material expanding the second chamber, but such ear canal seal is fragile and will not hold up to movement of the earphone and/or ear canal in response to movement of the user. Hence, the sealing material is forced into the second chamber in step 208 at least from the physical insertion of the tip into the ear and from the automatic elastic reaction of the material of the reservoir section of the deformable membrane.

The application of force from the automatic constriction of the reservoir section, as directed by the modulus of elasticity, in step 208, as illustrated in FIG. 3B, forces the sealing material into the second chamber and expands the sealing section outward into a forceful sealing contact with the ear canal. It is noted that there is a difference between the seal provided by the deformable membrane with and without the sealing material inflating the sealing section due to the sealing material continuously applying outward force on the deformable membrane toward the ear canal lining.

In some embodiments, step 208 involves a manual application of force to the reservoir section of the tip by a user in a manner other than with the modulus of elasticity of the deformable membrane. Such supplemental application of force can be done with a user's finger or with a mechanism, such as a knob or syringe, that is articulated to apply force. Decision 210 evaluates if more ear canal seal is desired. If so, step 212 manually applies force on the reservoir section of the tip to increase the amount of sealing material in the second chamber. Step 212 may alternatively be activated in order to increase pressure on the ear canal from the tip without actually increasing, or altering, the ear canal seal.

With the tip inflated with sealing material to create a robust ear canal seal, step 214 utilizes the earphone to play sound through the conduit of tip. In the event a tip is used as an ear plug or sound attenuating device, step 214 may alternatively block sound while sealing the ear canal. The robust ear canal seal provided by the inflated tip is dynamic and can maintain the seal despite movement of the earphone, user, and user's jaw due to the flow of sealing material between the respective tip chambers. For instance, the sealing section of the tip can dynamically adjust automatically between different diameters, and volumes of sealing material in the second chamber, in response to the user running, talking, and otherwise moving the ear canal. Hence, the tip changes the sealing section shape and size autonomously without the user directly touching, or otherwise activating, the tip.

At the conclusion of the sound reproduction, the user removes the earphone from the ear canal in step 216 with the tip inflated. That is, the tip can be removed from the ear canal efficiently and without pain while the sealing section is inflated by sealing material due to the sealing material flowing into the first chamber in response to tip movement during removal. As such, the user can enjoy the ear canal seal without concern that inadvertent earphone removal will result in pain and/or ear canal trauma that can accompany inflated mechanisms that are static or otherwise continuously inflated by a fluid pump.

Through the assorted embodiments of an earphone, a robust ear canal seal can be deployed. The ability to adjust the inflation of the sealing section of the tip with jaw movement allows a user to customize the comfort, fitment, and sound quality. The dynamic capability of the tip to automatically adapt to ear canal movement ensures that the ear canal seal is maintained with an inflated sealing section without causing discomfort to the user. As a result, the efficiency and comfort associated with earphone use is optimized.

What is claimed is:

1. An apparatus comprising:
    at least one audio transducing driver positioned within a housing;
    a tip attached to the housing and comprising a first chamber separated from a second chamber by a constriction ring, the constriction ring comprising a flexible band separated by a metering region, the metering region comprising a plurality of protrusions extending towards the flexible band and a deformable membrane; and
    a sealing material occupying portions of the first chamber and the second chamber, the plurality of protrusions configured to provide a predetermined flow rate of sealing material through the constriction ring.

2. The apparatus of claim 1, wherein the tip has an audio conduit continuously extending from the at least one audio transducing driver through the first and second chambers.

3. The apparatus of claim 1, wherein the first and second chambers are wholly contained within the tip.

4. The apparatus of claim 1, wherein a deformable membrane continuously extends to cover the first and second chambers.

5. The apparatus of claim 1, wherein the tip is configured to be positioned within the ear canal of a user.

6. The apparatus of claim 1, wherein the second chamber inflates to a sealing diameter in response to a first predetermined volume of sealing material being present in the second chamber.

7. The apparatus of claim 6, wherein the second chamber deflates to a reduced diameter in response to a second predetermined volume of sealing material being present in the second chamber.

8. The apparatus of claim 6, wherein the first chamber inflates to a reservoir diameter in response to the first predetermined volume of sealing material being present in the first chamber.

9. An earphone comprising:
    at least one audio transducing driver positioned within a housing having an audio nozzle;
    a tip attached to a retention feature of the audio nozzle and comprising a first chamber separated from a second chamber by a constriction ring, the constriction ring comprising a flexible band separated by a metering region, the metering region comprising a plurality of protrusions extending towards the flexible band and a deformable membrane; and
    a sealing material occupying portions of the first chamber and the second chamber, the plurality of protrusions configured to provide a predetermined flow rate of sealing material through the constriction ring.

10. The earphone of claim 9, wherein the tip is removeably attached to the audio nozzle.

11. The earphone of claim 9, wherein the retention feature comprises a groove and protrusion.

12. The earphone of claim 9, wherein the tip comprises a nozzle receiver having a matching shape and size to the retention feature.

13. The earphone of claim 9, wherein the tip comprises a first one-way valve and a second one-way valve.

14. A method comprising:
    attaching a tip to a housing, the housing containing at least one audio transducing driver;

squeezing a sealing section of the tip to force sealing material into a first chamber of the tip from a second chamber of the tip, the first chamber separated from the second chamber by a constriction ring the constriction ring comprising a flexible band separated by a metering region, the metering region comprising a plurality of protrusions extending towards the flexible band and a deformable membrane;

inserting the tip into an ear canal of a user; and flowing the sealing material into the second chamber in response to force applied by a reservoir section of a deformable membrane of the tip to inflate the sealing section to a sealing diameter that contacts and seals the ear canal, the plurality of protrusions configured to provide a predetermined flow rate of sealing material through the constriction ring.

15. The method of claim 14, further comprising altering the sealing diameter automatically in response to movement of the ear canal.

16. The method of claim 15, wherein the sealing diameter is altered by sealing material flowing through the constriction ring into the first chamber.

17. The method of claim 14, further comprising removing the tip from the ear canal while the sealing section is inflated to the sealing diameter.

* * * * *